(12) United States Patent
Ben-Nun

(10) Patent No.: US 8,313,450 B2
(45) Date of Patent: Nov. 20, 2012

(54) INFLATABLE COMPRESSION SLEEVE

(75) Inventor: Asher Ben-Nun, Carmiel (IL)

(73) Assignee: Mego Afek AC Ltd., Doar Afek (IL)

( * ) Notice: Subject to any disclaimer, the term of this patent is extended or adjusted under 35 U.S.C. 154(b) by 616 days.

(21) Appl. No.: 12/555,356

(22) Filed: Sep. 8, 2009

(65) Prior Publication Data

US 2009/0326576 A1    Dec. 31, 2009

Related U.S. Application Data

(63) Continuation-in-part of application No. 10/895,292, filed on Jul. 21, 2004, now abandoned.

(51) Int. Cl.
*A61H 7/00*   (2006.01)
*A61H 19/00*  (2006.01)
*A61F 5/00*   (2006.01)

(52) U.S. Cl. .......................... 602/23; 601/151

(58) Field of Classification Search ............. 601/27–32, 601/34, 148–152; 602/23, 27–30, 75
See application file for complete search history.

(56) References Cited

U.S. PATENT DOCUMENTS

| | | |
|---|---|---|
| 2,361,242 A | 10/1944 | Rosett |
| 3,867,939 A | 2/1975 | Moore et al. |
| 4,013,069 A | 3/1977 | Hasty |
| 4,066,084 A | 1/1978 | Tillander |
| 4,149,541 A | 4/1979 | Gammons et al. |
| 4,198,961 A | 4/1980 | Arkans |
| 4,338,923 A | 7/1982 | Gelfer et al. |
| 4,614,179 A | 9/1986 | Gardner et al. |
| 5,117,812 A | 6/1992 | McWhorter |
| 5,435,009 A | 7/1995 | Schild et al. |
| 5,443,488 A | 8/1995 | Namenye et al. |
| 5,489,259 A * | 2/1996 | Jacobs et al. ............ 602/13 |
| 5,625,556 A | 4/1997 | Janky et al. |
| 5,632,844 A | 5/1997 | Pate et al. |
| 5,741,295 A | 4/1998 | McEwen |
| 6,001,119 A | 12/1999 | Hampson et al. |
| 6,007,559 A | 12/1999 | Arkans |
| 6,010,470 A | 1/2000 | Albery et al. |
| 6,129,688 A | 10/2000 | Arkans |
| 6,203,510 B1 | 3/2001 | Takeuchi et al. |
| 6,322,530 B1 | 11/2001 | Johnson, Jr. et al. |
| 6,375,633 B1 * | 4/2002 | Endress et al. ............ 602/23 |
| 6,500,200 B1 | 12/2002 | Kushnir |
| 6,525,238 B2 | 2/2003 | Corrales |
| 6,682,547 B2 | 1/2004 | McEwen et al. |
| 6,846,295 B1 | 1/2005 | Ben-Nun |

FOREIGN PATENT DOCUMENTS

| | | |
|---|---|---|
| JP | 11292100 A | 10/1999 |
| JP | 2001178791 A | 7/2001 |
| JP | 2001333955 A | 12/2001 |
| WO | 03/007855 A1 | 1/2003 |

* cited by examiner

*Primary Examiner* — Kristen Matter
(74) *Attorney, Agent, or Firm* — Nath, Goldberg & Meyer; Jerald L. Meyer; Joshua B. Goldberg

(57) ABSTRACT

A disposable sleeve for compression therapy, with at least one inflatable air cell defined between a first airtight wall adjacent a patient's body to be treated and a second airtight wall. Each of the first and second walls includes an external porous layer and an internal layer including air-tight polyethylene (PE). The walls are bonded by molten portions of the PE internal layer penetrating and set in their corresponding external porous layers and welded to each other, the bonding enduring at least 250 inflation-deflation cycles associated with the therapy.

20 Claims, 3 Drawing Sheets

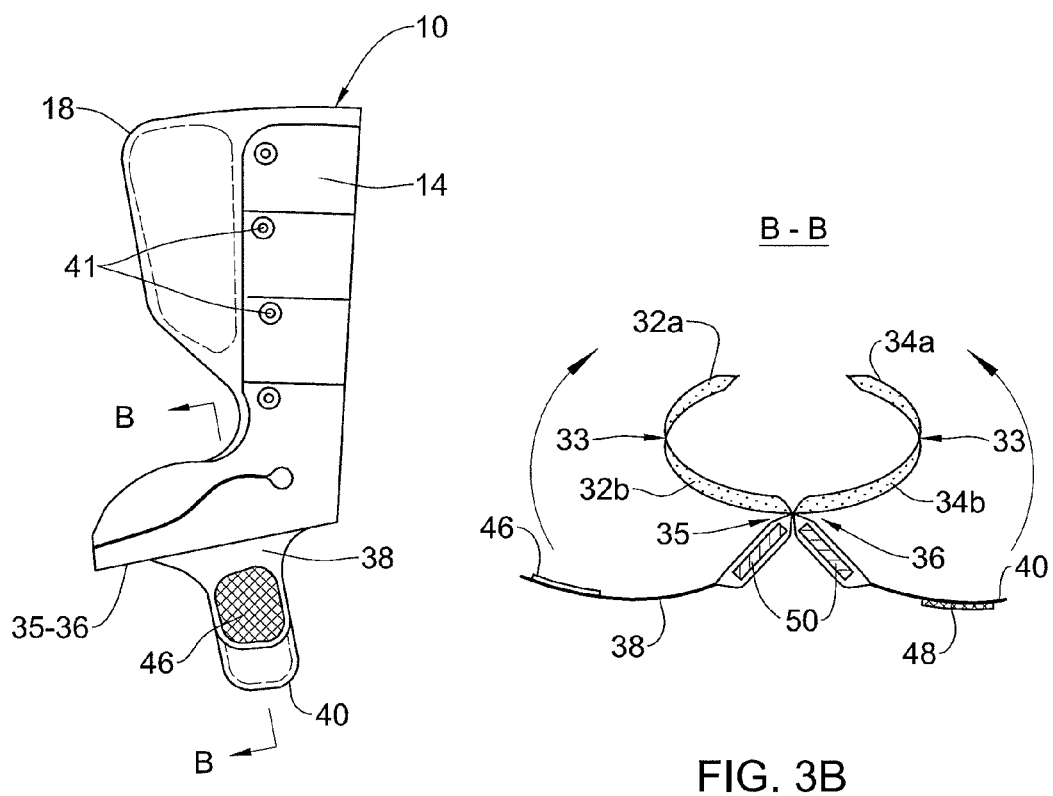
FIG. 3A
FIG. 3B
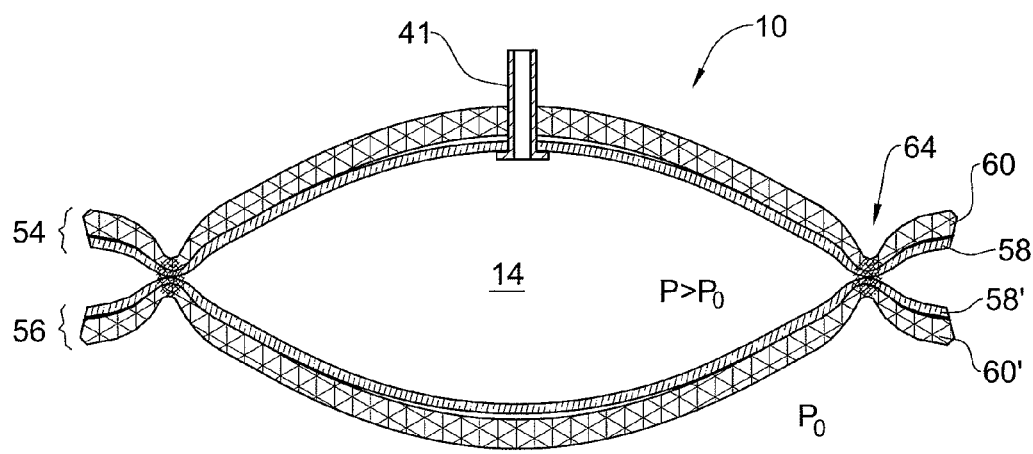
FIG. 4

INFLATABLE COMPRESSION SLEEVE

This application is a Continuation-in-Part of U.S. patent application Ser. No. 10/895,292, filed on Jul. 21, 2004, now abandoned.

FIELD OF THE INVENTION

This invention relates to inflatable sleeves for use in pneumatic compression therapy and to methods of producing such sleeves.

BACKGROUND OF THE INVENTION

Deep vein thrombosis, also known as DVT, is a serious and potentially life-threatening disorder. The physiological cause of this disorder is lack of adequate blood circulation in the lower extremities. The lack of movement of venous blood can cause clots to form, which may cause blockages in the local blood vessels, or in more serious situations, may lodge in the lungs or heart and cause critical blockages which can be life-threatening.

A large number of medical research studies have shown that deep vein thrombosis can be prevented by enhancing or accelerating the return of venous blood from the lower extremities. A common and accepted method for accelerating venous blood return from the lower limbs is pneumatic compression applied to the sole of the foot and/or the calf muscle of the leg. This form of treatment is commonly referred to as "compression therapy," and is performed using a compression device, which feeds compressed air to a garment or "sleeve" containing one or more cells which inflate and deflate, alternately applying and releasing pressure to the patient's lower extremities.

In hospitals, there are many devices of this kind, and there are compression therapy usage protocols for patients who are hospitalized for operative procedures or have other risk factors for developing deep vein thrombosis. The compression therapy devices may be used 24 hours a day for the entire hospitalization period. Clinical studies have shown that the effectiveness of such devices is primarily determined by patient and staff compliance, which in turn is affected by ease of use and patient comfort. The usage of such devices is also determined by economic factors such as cost of the device and garments as opposed to pharmaceutical interventions such as heparin.

U.S. Pat. No. 4,013,069 describes compression sleeves made of interior impervious sheets and one or more sheets of soft flexible material for covering the outside of the impervious sheets adjacent the patient's leg. The outer sheets may be made of any suitable material, such as TYVEK™, and they provide an aesthetically pleasing and comfortable outer surface for the sleeve. The outer sheets may be attached to the internal sheets by suitable means, such as stitches along the side and end edges. The sleeves may have a plurality of hook and loop strips to releasably secure the sleeves about the patient's legs.

U.S. Pat. No. 4,066,084 describes a cuff comprising a piece of stable fabric or plastic material of soft but not elastic quality, in the shape of a trapezium, the two non-parallel sides having the same length. The two non-parallel sides are provided with a divisible zip fastener, by means of which the cuff can be shaped to a slightly tapered cylinder fitting a patient's limb. On one side of the form-stable material, a number of elongated inflatable sections are provided arranged parallel to the parallel sides of the trapezium. These sections are manufactured of an elastic, strong plastic material, rubber or other air impervious material. The sections may also consist of balloons inserted in pockets in the cuff.

U.S. Pat. No. 4,338,923 describes a sleeve wrappable about the body part to be treated, made in the form of a substantially flat inflatable band divided into a plurality of internal inflatable cells extending annularly around the sleeve, in partially overlapping relationship. The band is made of three strips of resilient sheet material bonded to each other along spaced bond lines to define the partially overlapping inflatable cells.

The above-described sleeves for compression therapy are of durable construction and constitute a constant part of the massaging device that is used multiple times with different patients, mostly as physical therapy for chronic venous and lymphatic disorders.

When these devices are used as prophylaxis for deep vein thrombosis, either in the operating theater or during the recovery period, the specific needs of the hospital market are for disposable, one-time or one-patient use sleeves. Such made from PVC fabric are manufactured by the Kendall Co. (Tyco) as well as by other major manufacturers. However, the cost of these sleeves is still high, and hospitals have had to reprocess and reuse these so-called "disposable" sleeves in an attempt to cut expenses. In addition, PVC is now considered an environmentally "unfriendly" material, and its use has been curtailed in many countries because of concerns of carcinogenicity. The PVC outer layer also prevents normal evaporation of perspiration, causing discomfort to the patient.

SUMMARY OF THE INVENTION

The present invention is directed to a more hygienic disposable sleeve for one-time use, which is comfortable, reliable and inexpensive, and is particularly useful for massive usage of such devices in hospitals.

In accordance with the present invention, there is provided a disposable sleeve for compression therapy including a predetermined number of inflation-deflation cycles defining one use of the sleeve. The sleeve has at least one inflatable air cell defined between a first airtight wall to be located adjacent a patient's body to be treated and a second airtight wall. Each of the two walls comprises an external porous layer and an internal airtight layer comprising polyethylene (PE) adjacent the external layer, the internal layers facing each other. The walls are bonded along bonding seams by welding the internal layers to each other and by molten portions of the PE having penetrated and set in the external porous layers at said seams. The bonding and the walls are designed to endure at the predetermined number of inflation-deflation cycles. Preferably, this number is at least 250 cycles. For some applications, the bonding and the walls are adapted to endure about 30,000 cycles.

The internal layer may be made of reinforced PE, e.g. made of an intermediate reinforcing nylon sub-layer laminated between two PE sub-layers.

The external porous layer may be textile, preferably nonwoven, and may be made of polyester or polypropylene.

The disposable sleeve comprises a nipple for inflation of the air cell, with a collar welded to the internal layer of the first wall and bonded to the porous layer. The collar may be made of PE.

The disposable sleeve may comprise fastening means such as a flap for fixing the sleeve on a patient's body. The flap is preferably formed as an extension of the first and the second wall beyond the air cell. The flap preferably has means for attaching to another part of the sleeve, such as a male (hook) Velcro pad with backside laminated with PE. The pad is bonded by the backside to the external porous layer of the flap, the bonding constituting molten portion of the PE laminate, penetrating and set in the external porous layer, preferably reaching the internal PE layer and welded thereto.

The attaching means may further comprise a female pad including a layer of hook-holding material capable of holding hooks of the male Velcro pad and a layer of porous carrying material bonded to each other. The female pad is disposed between the first and said second wall of the flap and is bonded to the internal layer of the walls, the bonding constituting molten PE from the internal layer, penetrating and set in the porous materials of the female pad. One of the walls has a cut-out exposing the hook-holding material.

According to another aspect of the present invention, there is provided a method of producing the above-described compression therapy sleeve, the method comprising:

a) providing a first and a second airtight internal layers comprising PE, and a first and a second layer of porous material;

b) providing openings in the first internal layer and in the first layer of porous material, inserting a nipple for inflation of the air cell in said openings and welding said nipple to the first internal layer;

c) aligning the layers in a flat stack so that the two internal layers are sandwiched between the two layers of porous material;

d) bonding the flat stack of layers by pressing and melting locally the PE of the internal layers so that molten PE penetrates and sets in the porous material and welds to the adjacent internal layer, along seams defining the inflatable air cell, so that the bonding can endure the predetermined number of inflation-deflation cycles associated with the compression therapy.

When the therapy sleeve comprises a flap constituting an extension of the first and/or the second wall beyond the air cell, then the step (d) further includes bonding along seams defining the flap.

When the therapy sleeve comprises a male (hook) Velcro pad having backside laminated with PE, the step (c) further includes aligning the male pad on the flat stack adjacent the flap, while the step (d) further includes bonding the male pad to the flap by pressing and melting locally the backside PE laminate so that molten PE penetrates and sets in the porous material or welds to an adjacent internal layer.

When the therapy sleeve comprises a female pad including a layer of porous carrying material, step (c) further includes aligning the female pad in the flat stack adjacent an internal layer of the flap, while the step (d) further includes bonding the female pad to the flap by pressing and melting locally the PE in the internal layer of the flap so that molten PE penetrates and sets in the porous material of the female pad.

The step (d), including bonding of flaps and pads may be performed in one bonding stroke. The method may further include a cutting operation on the flat stack performed simultaneously with the bonding stroke.

The sleeve may comprise two parts to be used for treating different parts of the patient's body, for example the calf and the sole of the foot. The sleeve may have a stiffening member in a part thereof adjacent to the sole, preferably insertable in a pocket defined in such part of the sleeve, or bonded between the walls.

The compression therapy sleeve may comprise an arrangement of air cells adapted to be wrapped about a patient's limb, the air cells assuming generally annular form with an axis parallel to the limb. The air cell preferably form about two-thirds or less than a full annulus around a patient's limb of average girth, the fastening means completing the full annulus, whereby the sleeve is usable on limbs of different girth without overlapping of the air cells.

The disposable sleeve and the method of its production according to the invention provide for a very hygienic, friendly to human body, convenient and easy to use device for preventing and treating DVT and for massage therapy in general. The sleeve may be cheaply produced in mass quantities from common, inexpensive, more environmentally friendly plastic materials, using reliable technology with wide industrial application.

Usage of PE for air-tight welding or bonding is known for example from U.S. Pat. Nos. 6,500,200, 5,443,488 and 3,867,939. However, neither of these publications suggests multiple cyclic loading such as inflation-deflation therapy cycles.

BRIEF DESCRIPTION OF THE DRAWINGS

In order to understand the invention and to see how it may be carried out in practice, embodiments will now be described, by way of non-limiting examples only, with reference to the accompanying drawings, in which:

FIG. 3A is a side view of the sleeve of FIG. 1 in folded condition.

FIG. 3B is a cross-sectional view of the lower section of the sleeve of FIG. 3A.

FIG. 4 is a schematic cross-section through an air cell of the sleeve of FIG. 1.

DETAILED DESCRIPTION OF THE EMBODIMENTS

Figure 1:
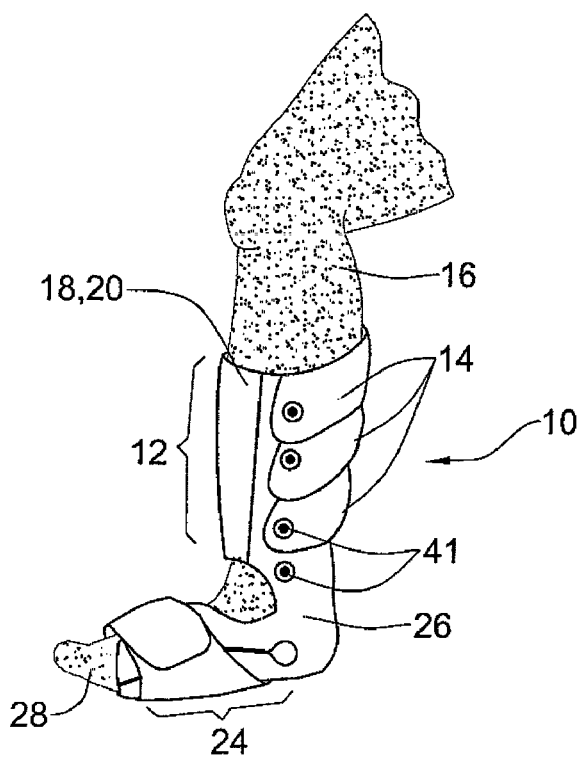
FIG. 1 is a view of a compression therapy sleeve according to an embodiment of the present invention, fixed in operative condition on a patient's lower limb.
Figure 2:
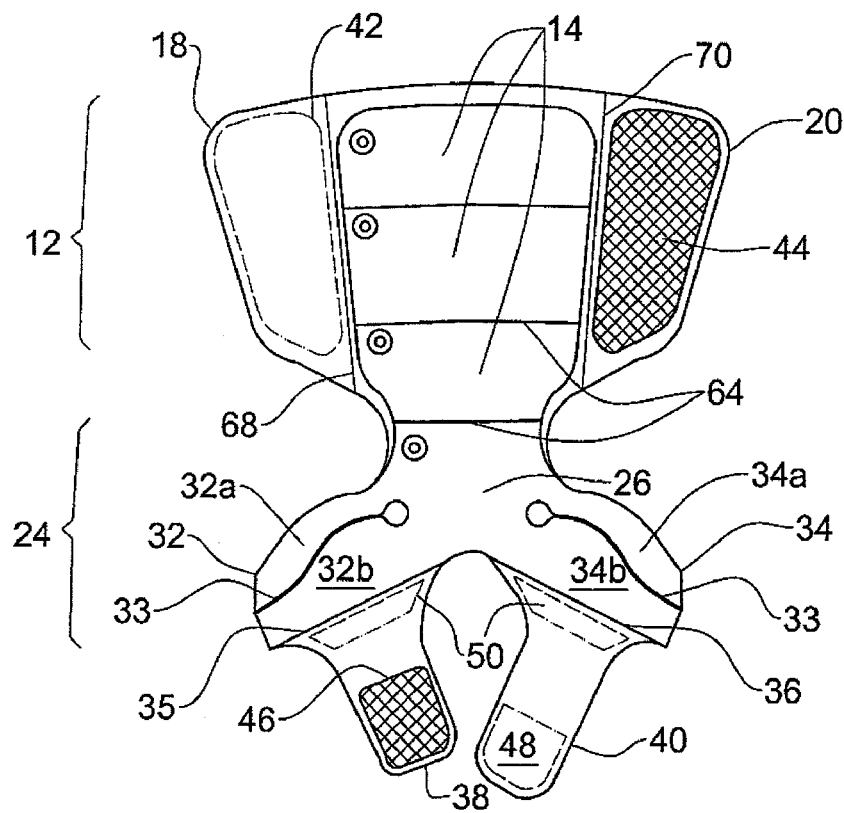
FIG. 2 is a plan view of the sleeve of FIG. 1 in flat condition.

With reference to FIGS. 1, 2 and 3, a disposable compression sleeve 10 in accordance with one embodiment of the present invention, designed for prevention of DVT, comprises an upper section 12 with upper air cells 14 for compressing the patient's calf 16, with upper fastening flaps 18 and 20 formed at left and right sides of the air cells 14; a lower section 24 with lower air cell 26 for compressing the sole 28 of the patient's foot, with lower fastening flaps 38 and 40; and air inlets (nipples) 41 in the air cells 14 and 26 mounted for connecting the air cells, by means of hoses, to an inflating device such as a compressor with distributor valve (not shown).

In the upper section 12, the size of the air cells 14 is not designed to cover only the calf muscle 16 rather than the whole circumference of the limb. The rest of the circumference is bridged by the fastening flaps 18 and 20, as explained below. The flaps 18 and 20 may be formed from the material of the air cells 14 or may be attached thereto along seams 68 and 70.

In the lower section 24, the lower air cell 26 has a left part 32 and right part 34 divided by seams 33 into respective upper lobes 32a and 34a, constituting an upper, instep portion, and respective lower lobes 32b and 34b, constituting a lower, sole portion. The air cell 26 has a left lower edge 35 and a right lower edge 36, shown unassembled in FIG. 2. In assembled state, the edges 35 and 36 are bonded together to form a common sole seam 35-36, whereby the lower lobes 32b and 34b form an inflatable sole, as shown in cross-section in FIG. 3B. The lower fastening flaps 38 and 40 are attached to the same edges 35 and 36. The fastening flaps may be formed integral with the lower section, from the sheet material of the sleeve. In such case, the edges 35 and 36 will be just seams between the air cell 26 and the flaps 38 and 40.

The upper section 12 and the lower section 24 of the sleeve 10 may be manufactured as one-piece garment but may be also separate and be used as two separate units.

In operative position, the sleeve 10 is placed against the foot of the patient with the upper section 12 behind the calf and the lower section 24 under the heel and sole of the foot. The air cells 14 are wrapped about the calf and fastened by means of the flaps 18 and 20. The lower section 24 is wrapped about the foot and fastened over the instep by means of flaps 38 and 40. Lobes 32b and 34b remain adjacent the sole of the foot while lobes 32a and 34a are adjacent the sides and the instep of the foot.

The fastening flaps 18, 20, 38 and 40 provide for closure and fastening of the sleeve around a wide range of limb girths without disrupting or affecting the air cells, thus eliminating the need for a variety of sizes for this sleeve. The fastening of the flaps may be realized by various means, for example hook and loop Velcro patches 42, 44, 46 and 48. Also, the fastening of the flaps may be effected by means of a self-adhesive layer on the flaps with the adhesive side protected by removable tape. Alternatively, a separate two-sided self-adhesive patch can be used, which can be placed on the sleeve by the patient or treatment personnel for closure according to the patient's limb exact size.

In another embodiment of the sleeve, the lower section 24 of the sleeve 10 may also contain rigid plates 50 (FIG. 2) built into the flaps 38 and 40, adjacent the seams 35 and 36, so as to support the lobes 32b and 34b that are in contact with the sole 28 of the foot. The rigid plates at the sole of the foot apply a force-resistant surface to the air cell, improving the efficiency of application of pressure to the sole of the foot. The rigid plates 50 may be insertable in pockets formed in the lower fastening flaps 38 and 40 adjacent the right and left lower lobes 32b and 34b of the lower air cell 26. In all the above cases, the rigid plate(s) 50 may be made of a stiff plastic, such as a board made of PVC, or other materials. When it is desired to prevent multiple use of the sleeve 10 and washing thereof required for such use, the plates 50 may be made of a material such as, for example, cardboard, which looses its rigidity when wetted.

With reference to the cross-section shown in FIG. 4, an air cell 14 or 26 in the sleeve 10 is formed with an upper wall 54 and a lower wall 56, where the lower wall 56 is adjacent the patient's limb when the sleeve is in use. The walls 54 and 56 comprise each a respective inner sheet 58, 58' and a respective outer sheet 60, 60' bonded together along lines 64, 68, 70, 33, 35, 36, etc. defining the contours of the air cells (only line 64 is seen in cross-section in FIG. 4). The inner sheets 58 and 58' are made of polyethylene, for example metallocene PE of Dow Chemicals, which is relatively cheap. The material is well weldable and airtight though not particularly strong. However, the inventors have tested and proved that, for example, a 100-150 μm sheet of this material has sufficient tensile strength and durability for a guaranteed limited number of inflation-deflation cycles. This number is typically about 30,000 for a few days of pre-surgery or post-surgery treatment of one patient. The number may be considerably less, about 250 for one or two procedures of compression therapy, which allows the usage of even thinner sheets of PE. The requirements to the cell walls strength may be further reduced if the cells do not embrace the whole circumference of the limb but about two-thirds or less. That is why, this material is very suitable for making disposable sleeves used for prevention of DVT in the limbs. The outer sheets 60 and 60' are made of porous material such as textile fabric. Preferably, non-woven textile is used, for example polypropylene or polyester fabric.

Figure 5:
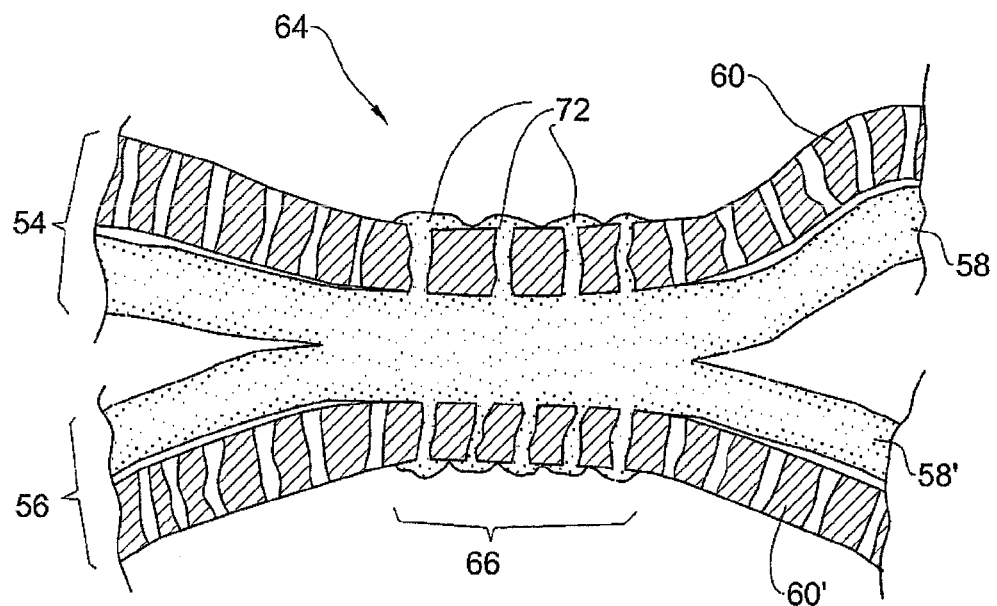
FIG. 5 is an enlarged cross-section of a welding zone in the sleeve of FIG. 4.

The bonding of the constituent sheets is done in a special way shown in FIG. 5. The two PE sheets 58, 58' are welded to each other, in a welding zone 66, for example by RF heating. At the same time, molten portions 72 of the PE in the welding zone 66 penetrate the pores of the porous material 60 and solidify there, locking the outer sheets 60, 60' to the PE sheets 58, 58' and to each other. Notably, the porous material need not be weldable to the PE layer. The inventors have discovered that such bonding may be sufficiently reliable and provides the required durability for the same number of cyclic inflations-deflations as above.

A method for production of the disposable compression therapy sleeve above includes the following steps:

a) providing an inner sheet 58 made of PE and an outer sheet 60 of porous material for the upper wall 54, cutting them to suitable form, aligning them and inserting air nipples 41 in openings of the sheets 58, 60;

b) bonding the air nipples 41 to the inner PE sheet and to the porous sheet 60;

c) providing an inner sheet 58' and an outer sheet 60' for the lower wall 56 and cutting them to a suitable form;

d) aligning the four sheets of material in a flat stack (Velcro pads, male and female, may be provided, with backside laminated with PE layer or with a porous layer, and aligned in the same flat stack. Also plates of stiff plastic 50 may be provided and inserted between the sheets);

e) bonding the stacked sheets across the stack along a pattern of seams 33, 35, 36, 64, 68, 70, etc. defining air cells 14 and 24;

f) folding the stack and bonding the left and right parts 32 and 34 of the lower air cell 26 together along their lower edges 35 and 36 to form a scoop-like accommodation for the heel of the foot, as shown in FIGS. 3A and 3B.

The fastening flaps 18, 20, 38 and 40 may be formed as extensions of the sleeve walls 54, 56 beyond the air cells so that the flaps will be obtained simultaneously with the air cells at step (e).

It is possible that all seams in the compression sleeve are obtained in one bonding stroke including welding, melting and setting. The bonding stroke may be combined with a cutting operation, for example, to obtain the outer contour of the sleeve.

Figure 6:
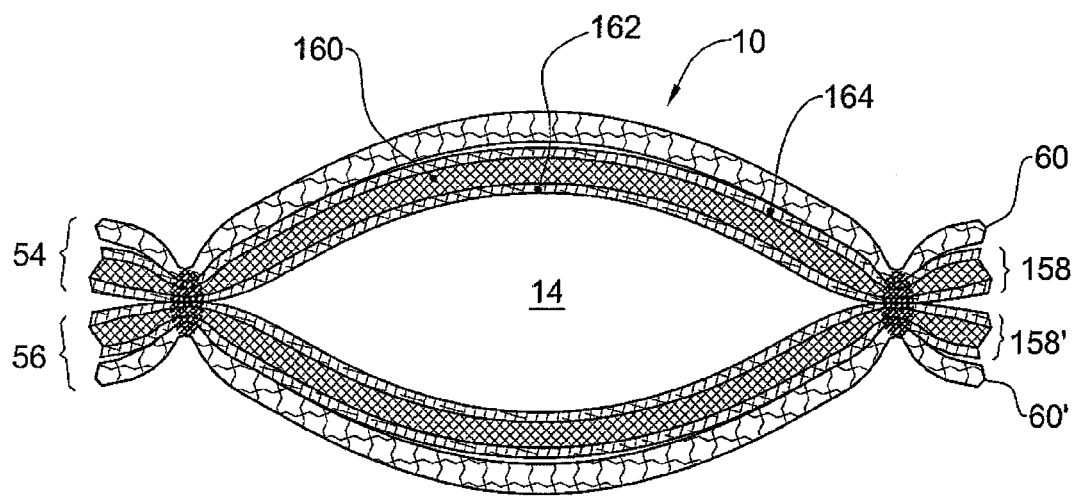
FIG. 6 is a schematic cross-section through an air cell of a sleeve according to another embodiment of the present invention.

As shown in FIG. 6, the compression therapy sleeve 10 may be made of reinforced inner sheets 158, 158' of more complex structure. The sheet 158 or 158' may comprise for example a reinforcing non-woven or nylon layer 160 sandwiched between two polyethylene layers 162 and 164, formed as an integral sheet, for example by lamination. Such materials are manufactured for use in the food packaging industry and are relatively cheap. The overall thickness of the inner sheets in this case may be even less than of a purely PE inner sheet. It will be appreciated that the same method of bonding as above can be applied.

Although a description of specific embodiment has been presented, it is contemplated that various changes could be made without deviating from the scope of the present invention. For example, the present invention could be modified and used for production of other compression devices for treating DVT or lymphedema.

The invention claimed is:

1. A sleeve for performing compression therapy on a patient, having an upper section for compressing the patient's calf, and a lower section for compressing the patient's foot, the sleeve, in its upper and lower sections, comprising:
   a first airtight wall to be located adjacent the patient's body to be treated;
   a second airtight wall;
   an internal layer in each of said first and said second airtight walls, made of an airtight material;
   an external layer in each of said first and second airtight walls, made of a porous material;

bonding seams along which the first and second airtight walls are welded to each other to form therebetween a plurality of air cells whose contour is defined by said seams and whose interior is defined by the internal layers facing each other; the plurality of air cells including upper air cells in said upper section of the sleeve and at least one lower air cell in said lower section of the sleeve, the lower air cell having a right and a left part each including an upper, instep portion and a lower, sole portion;

wherein the sole portions of the right and left parts of the lower air cell meet at a common sole seam;

the sleeve further comprises lower right and left fastening flaps extending from said common sole seam and configured to wrap about the sole and instep portions of the corresponding right and left part of the lower air cell, when the sleeve is in use and the lower air cell is inflated; and the right and left fastening flaps have respective right and left rigid plates located inside the flaps adjacent the common sole seam, configured to provide the sole portions of the right and left parts of the lower air cell with a force-resistant surface.

2. A sleeve according to claim 1, wherein the sleeve is disposable and the rigid plates are made of a material, which loses its rigidity when wetted or washed.

3. A sleeve according to claim 2, wherein the material from which the rigid plates are made is cardboard.

4. A sleeve according to claim 1, wherein the lower right and left fastening flaps are made of the same material as the lower section of the sleeve.

5. A sleeve according to claim 1, wherein the fastening flaps are formed by the extensions of the first and second airtight walls of the sleeve in its lower section.

6. A sleeve according to claim 1, wherein each of the right and left parts of the lower air cell comprises a side seam extending along a majority of the length of the sole seam and dividing each of the right and left parts into an upper lobe comprising the upper, instep portion of the lower air cell and a lower lobe comprising the lower, sole portion of the lower air cell.

7. A sleeve according to claim 1, wherein said airtight material of the internal layers of the first and second airtight walls includes a polyethylene (PE) layer, and at the area of the bonding seams, PE from said PE layer extends into pores in said porous material.

8. A sleeve according to claim 7, wherein the external layers of the first and second airtight walls each have an outer surface facing away from the corresponding internal layer, and the solidified PE projects from said outer surface at the area of the bonding seams.

9. A sleeve according to claim 8, wherein said material including PE, includes a single PE layer.

10. A sleeve according to claim 9, wherein in the area of said seam, the PE layers of the first and second airtight walls merge with each other.

11. A sleeve according to claim 10, wherein the PE from the merged PE layers extends into the pores of the porous material of the external layers, whereby a continuous PE area is formed extending between the pores of the two external layers along said seams through the entire thickness of the external layers.

12. A sleeve according to claim 11, wherein said PE that extends into the pores of the porous material projects outwardly therefrom.

13. A sleeve for performing compression therapy on a patient having an upper section for compressing the patient's calf, and a lower section for compressing the patient's foot, the sleeve, in its upper and lower sections, comprising:

a first airtight wall to be located adjacent the patient's body to be treated;

a second airtight wall;

an internal layer in each of said first and said second airtight walls, made of an airtight material;

an external layer in each of said first and second airtight walls, made of a porous material;

bonding seams along which the first and second airtight walls are welded to each other to form therebetween a plurality of air cells whose contour is defined by said seams and whose interior is defined by the internal layers facing each other; the plurality of air cells including upper air cells in said upper section of the sleeve and at least one lower air cell in said lower section of the sleeve; the lower air cell having a right and a left part each with an upper, instep portion and a lower, sole portion;

wherein the sole portions of the right and left parts of the lower air cell meet at common sole seam; the sleeve further comprises lower right and left fastening flaps extending from said common sole seam; and each of the right and left parts of the lower air cell comprises a side seam extending along a majority of the length of the sole seam and dividing each of the right and left parts into an upper lobe comprising the upper, instep portion of the lower air cell and a lower lobe comprising the lower, sole portion of the lower air cell.

14. A sleeve according to claim 13, wherein said airtight material of the internal layers of the first and second airtight walls includes a polyethylene (PE) layer; and at the area of the bonding seams, PE from said PE layer extends into pores in said porous material.

15. A sleeve according to claim 14, wherein PE from said PE layer extends into pores in said porous material also at the area of the side seam.

16. A sleeve according to claim 14, wherein the external layers of the first and second airtight walls each have an outer surface facing away from the corresponding internal layer, and the solidified PE projects from said outer surface at the area of the bonding seams.

17. A sleeve according to claim 14, wherein the material including PE includes a single PE layer.

18. A sleeve according to claim 14, wherein in the area of the bonding seams, the PE layers of the first and second airtight walls merge with each other.

19. A sleeve according to claim 18, wherein the PE from the merged PE layers extends into the pores of the porous material of the external layers, whereby a continuous PE area is formed extending between the pores of the two external layers along the bonding seams through the entire thickness of the external layers.

20. A sleeve according to claim 19, wherein said PE that extends into the pores of the porous material projects outwardly therefrom.

* * * * *